United States Patent
Rajasekhar et al.

(10) Patent No.: US 6,249,701 B1
(45) Date of Patent: Jun. 19, 2001

(54) IMPLANTABLE DEVICE WITH AUTOMATIC SENSING ADJUSTMENT

(75) Inventors: Suribhotla V. Rajasekhar, Santa Clara, CA (US); Girard B. Borgerding, Minneapolis; John G. Keimel, New Brighton, both of MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/250,065

(22) Filed: Feb. 12, 1999

(51) Int. Cl.$^7$ .................................................. A61N 1/362
(52) U.S. Cl. ............................................................ 607/9
(58) Field of Search ............................................ 607/9, 28

(56) References Cited

U.S. PATENT DOCUMENTS

| | | |
|---|---|---|
| 4,312,355 | 1/1982 | Funke . |
| 4,316,472 | 2/1982 | Mirowski et al. . |
| 4,375,817 | 3/1983 | Engle et al. . |
| 4,384,585 | 5/1983 | Zipes . |
| 4,577,633 | 3/1986 | Berkovits et al. . |
| 4,587,970 | 5/1986 | Holley et al. . |
| 4,726,380 | 2/1988 | Vollmann et al. . |
| 4,727,877 | 3/1988 | Kallok . |
| 4,800,883 | 1/1989 | Winstrom . |
| 4,830,006 | 5/1989 | Haluska et al. . |
| 4,880,005 | 11/1989 | Pless et al. . |
| 4,949,719 | 8/1990 | Pless et al. . |
| 4,953,551 | 9/1990 | Mehra et al. . |
| 5,027,815 | 7/1991 | Funke et al. . |
| 5,117,824 | 6/1992 | Keimel et al. . |
| 5,123,412 | 6/1992 | Betzold . |
| 5,188,105 | 2/1993 | Keimel . |
| 5,269,298 | 12/1993 | Adams et al. . |
| 5,269,300 | 12/1993 | Kelly et al. . |
| 5,545,186 | 8/1996 | Olson et al. . |
| 5,658,317 | 8/1997 | Haefner et al. .......................... 607/5 |
| 5,755,736 | 5/1998 | Gillberg et al. . |
| 5,755,738 * | 5/1998 | Kim et al. ................................ 607/9 |
| 5,941,830 * | 8/1999 | Williams ............................. 600/509 |
| B1 4,830,006 | 5/1989 | Haluska et al. . |
| B1 4,880,005 | 11/1989 | Pless et al. . |

FOREIGN PATENT DOCUMENTS 9218198  10/1992  (WO) .

OTHER PUBLICATIONS

"Automatic Tachycardia Recognition", by Arzbaecher et al., published in PACE, May–Jun., 1984, pp. 541–547.
"Onset and Stability for Ventricular Tachyarrhythmia Detection in an Implantable Pacer–Cardioverter–Defibrillator" by Olson et al., published in *Computers in Cardiology*, Oct. 7–10, 1986, IEEE Computer Society Press, pp. 167–170.
Application Ser. No. 09/112,917, by Borgerding et al. for an Implantable Device With Automatic Sensing Adjustment, filed by Jul. 9, 1998.

* cited by examiner

Primary Examiner—William E. Kamm
(74) Attorney, Agent, or Firm—Reed A. Duthler; Girma Wolde-Michael (57) ABSTRACT

A system and method is provided to view an anatomical structure such as a blood vessel in high contrast with its surrounding tissue. The system and method may be used to produce an image of an anatomical structure using reflected electromagnetic radiation singularly scattered from target tissue. The system and method may also provide same-side illumination and detection of reflected electromagnetic radiation in a convenient integral imaging device. The system and method may also provide helmet mounted imaging technology in a single integral helmet which allows the wearer to view an anatomical structure located within a patient such that the image is continuously oriented according to the orientation of the helmet wearer's head. The system and method may also be used in the performance of venipuncture. The system and method may provide for improved contrast between any anatomical structure and its surrounding tissue for use in any imaging system.

16 Claims, 7 Drawing Sheets

IMPLANTABLE DEVICE WITH AUTOMATIC SENSING ADJUSTMENT

CROSS REFERENCE TO RELATED APPLICATION

Reference is made to U.S. patent application Ser. No. 09/112,917 now U.S. Pat. No. 6,058,327, by Borgerding et al. for an IMPLANTABLE DEVICE WITH AUTOMATIC SENSING ADJUSTMENT, filed Jul. 9, 1998, which contains subject matter related to that of the present application.

BACKGROUND OF THE INVENTION

The present invention relates to medical stimulators and leads generally, and more particularly to implantable pacemakers, cardioverters and defibrillators.

In the context of implantable pacemakers or other stimulators which stimulate and sense electrical activity in multiple chambers of the heart, it has been conventional to provide a blanking period for the amplifier associated with one chamber of the heart, during delivery of a pacing pulse to another chamber of the heart. An earlier example of this feature may be found in U.S. Pat. No. 4,312,355 issued to Funke. It is also conventional to provide a blanking period for the sense amplifier coupled to the chamber being paced, during delivery of the pacing pulse and to provide atrial refractory and/or blanking periods associated with sensed ventricular depolarizations, as in U.S. Pat. No. 5,027,815, issued to Funke and U.S. Pat. No. 5,123,412, issued to Betzold.

Particularly in the context of devices which detect tachyarrhythmias, amplifiers have been developed which automatically adjust the effective sensing threshold, in order to facilitate sensing of the relatively lower amplitude depolarization wave forms that may be associated with tachyarrhythmias without sensing the repolarization wave forms associated with depolarizations occurring during normal sinus rhythm. The adjusting of the effective sensing threshold may be accomplished by adjusting the gain of the amplifier and comparing the amplified signal to a fixed threshold and/or by adjusting the threshold level of the detector associated with the amplifier, which adjustments should be understood to be equivalent alternatives in the context of the present invention. One such auto-adjusting amplifier is disclosed in U.S. Pat. No. 5,117,824 issued to Keimel et al, incorporated herein by reference in its entirety. An alternative implementation of an auto adjust amplifier is disclosed in U.S. Pat. No. 5,269,300 issued to Kelly et al., also incorporated herein by reference in its entirety. In these references, following a detected depolarization, the amplifier is automatically adjusted so that the effective sensing threshold is set to be equal to a predetermined portion of the amplitude of the sensed depolarization, and the effective sensing threshold decays thereafter to a lower or base sensing threshold. Following delivery of a pacing pulse, in the system disclosed in the Keimel et al patent, no adjustment is made to the sensing threshold, while in the Kelly et al. patent, following delivery of a pacing pulse the effective sensing threshold is set to a preset value and remains at this value for a defined period of time, after which the threshold decays to the lower or base value.

In the context of a device which paces and senses in multiple chambers of the heart, employing blanking and refractory periods as described above, alone or in conjunction with auto adjusting amplifiers as described above, does provide a useful and workable device. However, this approach does not address the difficulties which arise when the signal associated with a depolarization in the ventricle is of sufficient amplitude to be sensed by the atrial sense amplifier, commonly referred to as far-field R-wave sensing. This problem is addressed to some extent by provision of atrial blanking or refractory periods following sensing in the ventricle, but at the cost of the ability to accurately respond to atrial depolarizations occurring within these periods. In addition, the far-field R-wave may sometimes be sensed in the atrium before the R-wave is sensed by the ventricular sense amplifier, prior to initiation of blanking or refractory periods associated with the R-wave.

SUMMARY OF THE INVENTION

The present invention addresses the problem of far field R-wave sensing by defining a time window associated with a ventricular event (sensed or paced R-wave) during which far field R-wave sensing is likely to occur (hereafter referred to as the "far-R window") and by automatically increasing the atrial sensing threshold following a ventricular event until the expiration of the far-R window. The atrial sensing threshold is adjusted from a programmed base sensing threshold to a level which will allow for appropriate sensing of P-waves in the atrium while preventing inappropriate sensing of far field R-waves. The atrial sensing threshold may be adjusted as a function of the amplitude of one or more preceding P-waves as sensed by the atrial sense amplifier. Only sensed atrial events which exceed this increased sensing threshold are classified as P-waves.

In one embodiment of the invention, the adjustment of the sensing threshold is accomplished in a hardware implementation, in which the atrial sensing threshold following a ventricular event preceded by a sensed P-wave is adjusted to a level selected as a function of the amplitude of the preceding sensed P-wave. In this embodiment, the atrial sensing threshold following a ventricular event preceded by a delivered atrial pacing pulse is adjusted to a level selected as a function of the programmed base sensing threshold. In a second, software based embodiment, the device defines a minimum amplitude which a sensed atrial event must exceed to be classified as a P-wave or more preferably a range of amplitudes in which a sensed atrial event must fall to be classified as a P-wave. The minimum amplitude or the range of amplitudes is set as a function of the amplitudes of previously sensed P-waves. In both embodiments, the device preferably employs only the amplitudes of sensed atrial events which are classified as P-waves for purposes of defining the sensing threshold or range of amplitudes indicative of a sensed P-wave.

The present invention may be employed in the context of any implantable pacemaker which senses and/or paces in both the atrium and ventricle, including pacemakers capable of pacing in DDD, DDDR, VDD, VDDR, DDI, DDIR and VAT modes. The invention is particularly desirable in the context of a device such as a pacemaker/cardioverter/defibrillator which detects and/or treats atrial and/or ventricular arrhythmias.

DETAILED DESCRIPTION OF THE PREFERRED EMBODIMENT

Figure 1:
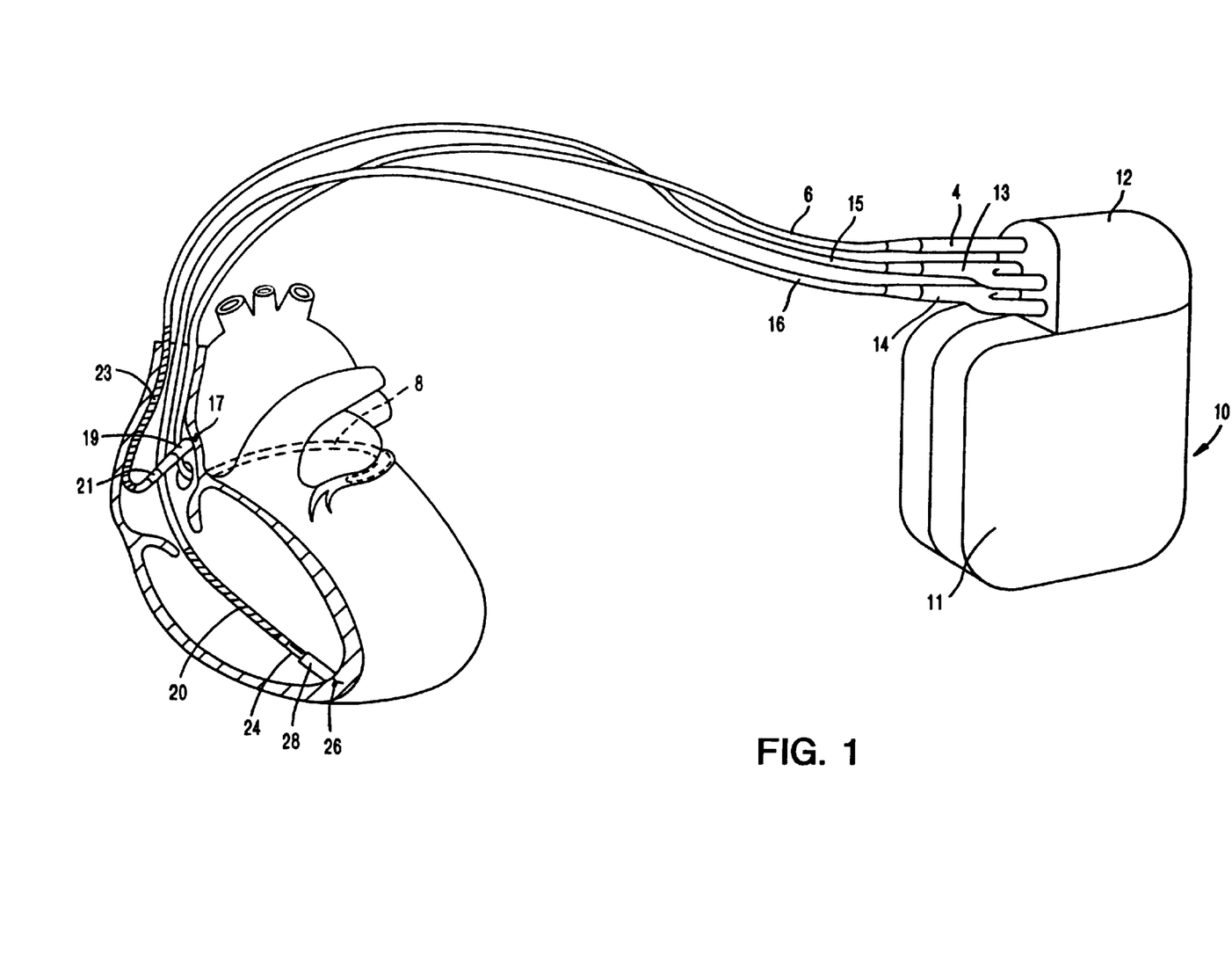
FIG. 1 illustrates a first embodiment of an implantable defibrillator and lead according to the present invention.

FIG. 1 illustrates a pacemaker/cardioverter/defibrillator and lead set according to the present invention. The ventricular lead includes an elongated insulative lead body 16, carrying three mutually insulated conductors. Located adjacent the distal end of the lead are a ring electrode 24, an extendable helix electrode 26, mounted retractably within an insulative electrode head 28, and an elongated coil electrode 20. Each of the electrodes is coupled to one of the conductors within the lead body 16. Electrodes 24 and 26 are employed for cardiac pacing and for sensing ventricular depolarizations. At the proximal end of the lead is a bifurcated connector assembly 14 which carries three electrical connectors, each coupled to one of the conductors. The defibrillation electrode 20 may be fabricated from platinum, platinum alloy or other materials known to be usable in implantable defibrillation electrodes and may be about 5 cm in length.

The atrial/SVC lead includes an elongated insulative lead body 15, carrying three mutually insulated conductors, corresponding generally to the structure of the ventricular lead. Located adjacent the J-shaped distal end of the lead are a ring electrode 21 and an extendable helix electrode 17, mounted retractably within an insulative electrode head 19. Each of the electrodes is coupled to one of the conductors within the lead body 15. Electrodes 17 and 21 are employed for atrial pacing and for sensing atrial depolarizations. An elongated coil electrode 23 is provided, proximal to electrode 21 and coupled to the third conductor within the lead body 15. Electrode 23 preferably is 5–10 cm in length or greater and is configured to extend from the SVC toward the tricuspid valve. In one preferred embodiment tested by the inventors, approximately 5 cm of the right atrium/SVC electrode was located in the right atrium, with the remaining 5 cm located in the SVC. At the proximal end of the lead is a bifurcated connector assembly 13 which carries three electrical connectors, each coupled to one of the coiled conductors.

The coronary sinus lead includes an elongated insulative lead body 6, carrying one conductor, coupled to an elongated coiled defibrillation electrode 8. Electrode 8, illustrated in broken outline, is located within the coronary sinus and great vein of the heart. At the proximal end of the lead is a connector assembly 4 which carries an electrical connector, coupled to the conductor in lead body 6. The coronary sinus/great vein electrode 8 may be about 5 cm in length.

An implantable pacemaker/cardioverter/defibrillator 10 is shown in combination with the leads, with the lead connector assemblies 4, 13 and 14 inserted into the connector block 12. Optionally, insulation of the outward facing portion of the housing 11 of the pacemaker/cardioverter/defibrillator 10 may be provided using a plastic coating, for example parylene or silicone rubber, as is currently employed in some unipolar cardiac pacemakers. However, the outward facing portion may instead be left uninsulated, or some other division between insulated and uninsulated portions may be employed. The uninsulated portion of the housing 11 optionally serves as a subcutaneous defibrillation electrode, used to defibrillate either the atria or ventricles.

Figure 2:
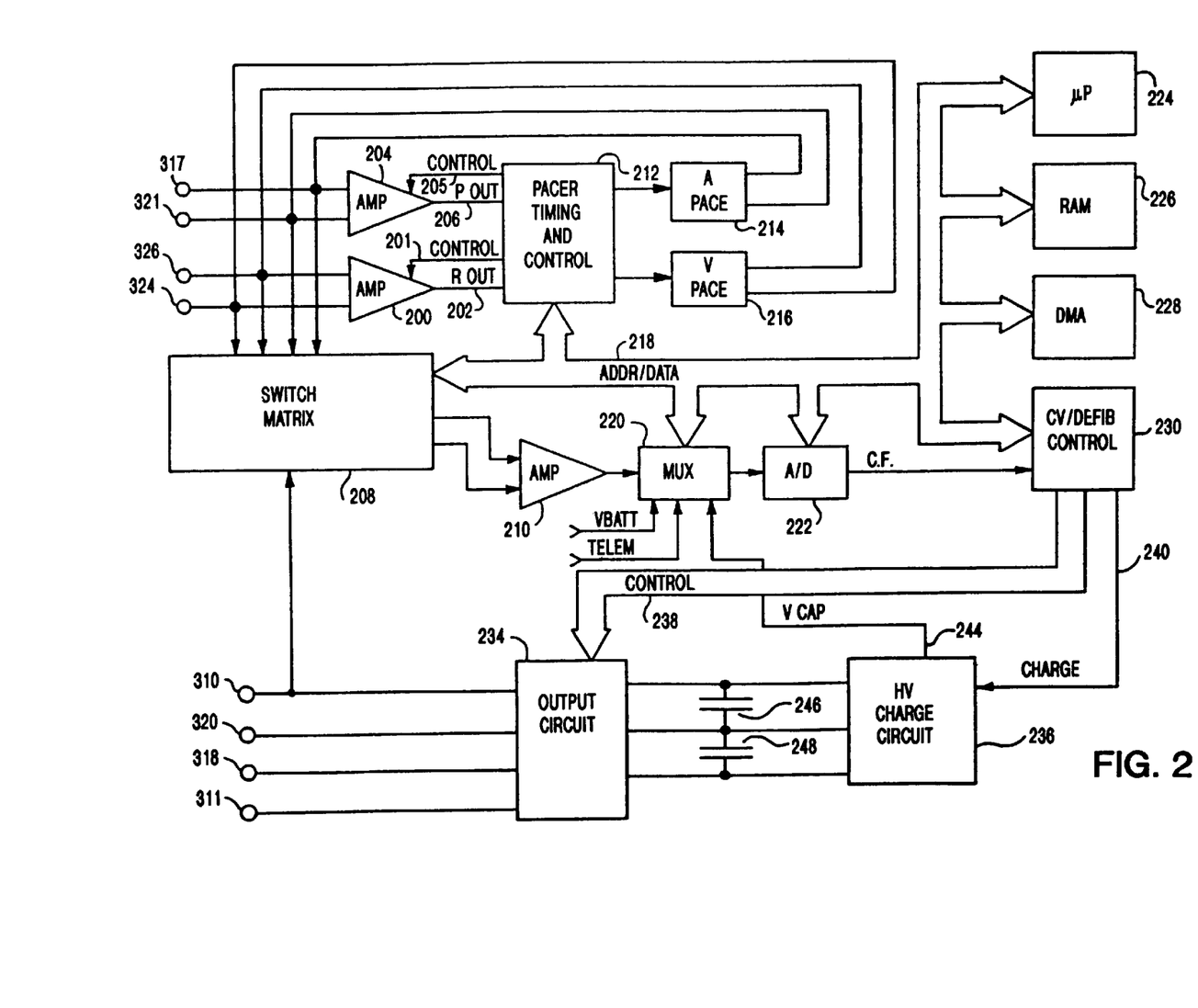
FIG. 2 is a functional schematic diagram of an implantable pacemaker/cardioverter/defibrillator in which the invention may usefully be practiced.

FIG. 2 is a functional schematic diagram of an implantable pacemaker/cardioverter/defibrillator in which the present invention may usefully be practiced. This diagram should be taken as exemplary of one type of device in which the invention may be embodied, and not as limiting, as it is believed that the invention may usefully be practiced in a wide variety of device implementations, including cardiac pacemakers which do not provide high voltage cardioversion and defibrillation therapies.

The device as illustrated is provided with an electrode system including electrodes as illustrated in FIG. 1. The correspondence to the illustrated electrodes is as follows. Optional electrode 310 corresponds to the uninsulated portion of the housing 11 of the implantable pacemaker/cardioverter/defibrillator. Electrode 320 corresponds to electrode 20 and is a defibrillation electrode located in the right ventricle. Electrode 311 corresponds to electrode 23, and is located in the right atrium and/or SVC. Electrode 318 corresponds to electrode 8 and is a defibrillation electrode located in the coronary sinus and great vein. Electrodes 324 and 326 correspond to electrodes 24 and 26, and are used for sensing and pacing in the ventricle. Electrodes 317 and 321 correspond to electrodes 17 and 19 and are used for pacing and sensing in the atrium.

Electrodes 310, 311, 318 and 320 are coupled to high voltage output circuit 234. High voltage output circuit 234 includes high voltage switches controlled by CV/defib control logic 230 via control bus 238. The switches within circuit 234 control which electrodes are employed and which are coupled to the positive and negative terminals of the capacitor bank including capacitors 246 and 248 during delivery of the defibrillation pulses.

Electrodes 324 and 326 are located on or in the ventricle and are coupled to the R-wave amplifier 200, which preferably takes the form of an automatically adjusted amplifier according to the above-cited application by Borgerding et al., incorporated herein by reference in its entirety and corresponding to the operation of the sense amplifiers in Medtronic Model 7250 and Model 7271 implantable pacemaker/cardioverter/defibrillators. The R-wave amplifier 200 provides an adjustable sensing threshold as a function of the measured R-wave amplitude and provides an increased sensing threshold following pacing pulses delivered to the atrium. Operation of amplifier 200 is controlled by pacing circuitry 212 via control lines 201. A signal is generated on R-out line 202 whenever the signal sensed between electrodes 324 and 326 exceeds the present sensing threshold.

Electrodes 317 and 321 are located on or in the atrium and are coupled to the P-wave amplifier 204, which in the hardware based implementation of the present invention preferably also takes the form of an automatically adjusted amplifier providing an adjustable sensing threshold following R-waves sensed by amplifier 200 as a function of a previously measured P-wave amplitude and also providing an increased sensing threshold following pacing pulses delivered to the ventricle. Operation of amplifier 204 is controlled by pacing circuitry 212 via control lines 205. A signal is generated on P-out line 206 whenever the signal sensed between electrodes 317 and 321 exceeds the present sensing threshold. The operation of amplifier 204 is discussed in more detail below in conjunction with FIGS. 3, 4 and 5.

Switch matrix 208 is used to select which of the available electrodes are coupled to wide band (0.25–100 Hz) amplifier 210 for use in digital signal analysis. Selection of electrodes is controlled by the microprocessor 224 via data/address bus 218, which selections may be varied as desired. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal processing methodologies known to the art.

The remainder of the circuitry is dedicated to the provision of cardiac pacing, cardioversion and defibrillation therapies, and, for purposes of the present invention may correspond to circuitry known in the prior art. An exemplary apparatus is disclosed of accomplishing pacing, cardioversion and defibrillation functions follows. The pacer timing/control circuitry 212 includes programmable digital counters which control the basic time intervals associated with DDD, VVI, DVI, VDD, AAI, DDI and other modes of single and dual chamber pacing well known to the art. Circuitry 212 also controls escape intervals associated with anti-tachyarrhythmia pacing in both the atrium and the ventricle, employing any anti-tachyarrhythmia pacing therapies known to the art.

Intervals defined by pacing circuitry 212 include atrial and ventricular pacing escape intervals, the refractory periods during which sensed P-waves and R-waves are ineffective to restart timing of the escape intervals and the pulse widths of the pacing pulses and all intervals associated with the automatic adjustments of effective sensing thresholds discussed in more detail below. The durations of these intervals are determined by microprocessor 224, in response to stored data in memory 226 and are communicated to the pacer timing/control circuitry 212 via address/data bus 218. Circuitry 212 also determines the amplitudes of the cardiac pacing pulses under control of microprocessor 224.

During pacing, the escape interval counters within pacer timing/control circuitry 212 are reset upon sensing of R-waves and P-waves as indicated by signals on lines 202 and 206, and in accordance with the selected mode of pacing on time-out trigger generation of pacing pulses by pacer output circuits 214 and 216, which are coupled to electrodes 317, 321, 324 and 326. The escape interval counters are also reset on generation of pacing pulses, and thereby control the basic timing of cardiac pacing functions, including anti-tachyarrhythmia pacing. The durations of the intervals defined by the escape interval timers are determined by microprocessor 224, via data/address bus 218. The value of the count present in the escape interval counters when reset by sensed R-waves and P-waves may be used to measure the durations of R-R intervals, P-P intervals, P-R intervals and R-P intervals, which measurements are stored in memory 226 and used to detect the presence of tachyarrhythmias.

Microprocessor 224 operates as an interrupt driven device, under control of a stored program in its read only memory and is responsive to interrupts from pacer timing/control circuitry 212 corresponding to the occurrence sensed P-waves and R-waves and corresponding to the generation of cardiac pacing pulses. These interrupts are provided via data/address bus 218. Any necessary mathematical calculations to be performed by microprocessor 224 and any updating of the values or intervals controlled by pacer timing/control circuitry 212 take place following such interrupts.

For example, in response to a sensed or paced ventricular depolarization or R-wave, the intervals separating that R-wave from the immediately preceding R-wave, paced or sensed (R-R interval) and the interval separating the paced or sensed R-wave from the preceding atrial depolarization, paced or sensed (P-R interval) may be stored. Similarly, in response to the occurrence of a sensed or paced atrial depolarization (P-wave), the intervals separating the sensed P-wave from the immediately preceding paced of sensed atrial contraction (P-P interval) and the interval separating the sensed P-wave from the immediately preceding sensed or paced ventricular depolarization (R-P interval) may be stored. Preferably, a portion of the memory 226 (FIG. 4) is configured as a plurality of recirculating buffers, capable of holding a preceding series of measured intervals, which may be analyzed in response to the occurrence of a pace or sense interrupt to determine whether the patient's heart is presently exhibiting atrial or ventricular tachyarrhythmia.

Detection of atrial or ventricular tachyarrhythmias, as employed in the present invention, may correspond to tachyarrhythmia detection algorithms known to the art. For example, presence of atrial or ventricular tachyarrhythmia may be confirmed by means of detection of a sustained series of short R-R or P-P intervals of an average rate indicative of tachyarrhythmia or an unbroken series of short R-R or P-P intervals. The suddenness of onset of the detected high rates, the stability of the high rates, or a number of other factors known to the art may also be measured at this time. Appropriate ventricular tachyarrhythmia detection methodologies measuring such factors are described in U.S. Pat. No. 4,726,380, issued to Vollmann, U.S. Pat. No. 4,880,005, issued to Pless et al. and U.S. Pat. No. 4,830,006, issued to Haluska et al., all incorporated herein by reference in their entireties. An additional set of tachycardia recognition methodologies is disclosed in the article "Onset and Stability for Ventricular Tachyarrhythmia Detection in an Implantable Pacer-Cardioverter-Defibrillor" by Olson et al., published in *Computers in Cardiology*, Oct. 7–10, 1986, IEEE Computer Society Press, pages 167–170, also incorporated herein in its entirety. Atrial fibrillation detection methodologies in particular are disclosed in Published PCT Application Ser. No. US 92/02829, Publication No. WO 92/18198, by Adams et al., and in the article "Automatic Tachycardia Recognition", by Arzbaecher et al., published in PACE, May-June, 1984, pp. 541–547, both of which are incorporated by reference in their entireties. Particularly appropriate hierarchical rule-based tachyarrhythmia detection and classification methodologies for use in conjunction with a device as illustrated in FIG. 2 are set forth in U.S. Pat. No. 5,545,186, by Olson et al. and in U.S. Pat. No. 5,755,736, by Gillberg et al., both incorporated herein by reference in their entireties. However, one of the advantages of the present invention is that it is believed practicable in conjunction with most prior art tachycardia detection algorithms.

Because the accurate detection of arrhythmias using measured intervals between R-waves and P-waves is dependent on accurate sensing of the occurrences of these depolarization signals, the automatic effective sensing threshold adjustment provided by the present invention is particularly valuable in the context of anti-tachyarrhythmia devices. However, the improved sensing accuracy is also valuable in the context of anti-bradycardia pacemakers as well, particularly in the context of mode-switching features intended to prevent such pacemakers from pacing the heart at inappropriately high rates.

In the event that an atrial or ventricular tachyarrhythmia is detected, and an anti-tachyarrhythmia pacing regimen is desired, appropriate timing intervals for controlling generation of anti-tachyarrhythmia pacing therapies are loaded from microprocessor 224 into the pacer timing and control circuitry 212, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 4,726,380, issued to Vollmann et al. on Feb. 23, 1988 and U.S. Pat. No. 4,587,970, issued to Holley et al. on May 13, 1986, all of which are incorporated herein by reference in their entireties may also be used.

In the event that generation of a cardioversion or defibrillation pulse is required, microprocessor 224 employs an escape interval counter to control timing of such cardioversion and defibrillation pulses, as well as associated refractory periods. In response to the detection of atrial or ventricular fibrillation or tachyarrhythmia requiring a cardioversion pulse, microprocessor 224 activates cardioversion/defibrillation control circuitry 230, which initiates charging of the high voltage capacitors 246 and 248 via charging circuit 236, under control of high voltage charging control lines 240 and 242. The voltage on the high voltage capacitors is monitored via VCAP line 244, which is passed through multiplexer 220 and in response to reaching a predetermined value set by microprocessor 224, results in generation of a logic signal on Cap Full (CF) line 254, terminating charging. Thereafter, timing of the delivery of the defibrillation or cardioversion pulse is controlled by pacer timing/control circuitry 212. Following delivery of the fibrillation or tachycardia therapy the microprocessor then returns the device to cardiac pacing and awaits the next successive interrupt due to pacing or the occurrence of a sensed atrial or ventricular depolarization.

One embodiment of an appropriate system for delivery and synchronization of ventricular cardioversion and defibrillation pulses and for controlling the timing functions related to them is disclosed in more detail in commonly assigned U.S. Pat. No. 5,188,105 by Keimel, issued Feb. 23, 1993, incorporated herein by reference in its entirety. Embodiments of appropriate systems for delivery and synchronization of atrial cardioversion and defibrillation pulses and for controlling the timing functions related to them are disclosed in more detail in U.S. Pat. No. 5,269,298 by Adams et al., issued Dec. 14, 1993 and in U.S. Pat. No. 4,316,472 by Mirowski et al., issued Feb. 23, 1982, both incorporated herein by reference in their entireties. However, any known cardioversion or defibrillation pulse control circuitry is believed usable in conjunction with the present invention. For example, circuitry controlling the timing and generation of cardioversion and defibrillation pulses as disclosed in U.S. Pat. No. 4,384,585, issued to Zipes on May 24, 1983, in U.S. Pat. No. 4,949,719 issued to Pless et al., cited above, and in U.S. Pat. No. 4,375,817, issued to Engle et al., all incorporated herein by reference in their entireties may also be employed.

In the illustrated device, delivery of the cardioversion or defibrillation pulses is accomplished by output circuit 234, under control of control circuitry 230 via control bus 238. Output circuit 234 determines whether a monophasic or biphasic pulse is delivered, the polarity of the electrodes and which electrodes are involved in delivery of the pulse. Output circuit 234 also includes high voltage switches which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuitry for delivery of biphasic pulse regimens to multiple electrode systems may be found in the above cited patent issued to Mehra and in U.S. Pat. No. 4,727,877, incorporated by reference in its entirety.

An example of circuitry which may be used to control delivery of monophasic pulses is set forth in commonly assigned U.S. Pat. No. 5,163,427, by Keimel, issued Nov. 17, 1992, also incorporated herein by reference in its entirety. However, output control circuitry as disclosed in U.S. Pat. No. 4,953,551, issued to Mehra et al. on Sept. 4, 1990 or U.S. Pat. No. 4,800,883, issued to Winstrom on Jan. 31, 1989 both incorporated herein by reference in their entireties, may also be used in conjunction with a device embodying the present invention for delivery of biphasic pulses.

In the event that, as in FIG. 1, both atrial and ventricular defibrillation are available, ventricular defibrillation may be accomplished using higher pulse energy levels than required for atrial defibrillation and may employ the same or a different electrode set. For example, electrodes 310, 311, 318 and 320 or only electrodes 311, 318 and 320 may be employed for atrial defibrillation. Electrodes 311, 320 and 310 might be employed for ventricular defibrillation, with electrode 311 (right atrium/SVC) coupled to electrode 310 (device housing). Alternatively, electrodes 310, 318 and 320 may be employed, with electrode 318 (coronary sinus/great vein) coupled to electrode 310. As a further alternative, electrodes 311, 310, 318 and 323 might all be employed for ventricular defibrillation, with electrodes 310, 311 and 323 coupled in common. As yet another alternative, only electrodes 310 and 320 might be employed for ventricular defibrillation added or substituted for either of electrodes 311 or 318 for treating ventricular fibrillation.

One particularly desirable embodiment of the invention employs only the right atrial/SVC electrode 311, the coronary sinus/great vein electrode 318 and the right ventricular electrode 320. During atrial defibrillation, electrodes 320 and 318 are coupled in common with one another, and the atrial defibrillation pulse is delivered between these electrodes and electrode 311. During ventricular defibrillation, electrodes 311 and 318 are coupled in common with one another, and the ventricular defibrillation pulse is delivered between these electrodes and electrode 320. This particular set of electrodes thus provides optimized defibrillation pulse regimens for both atrial and ventricular defibrillation, by simply switching the connection of the coronary sinus/great vein electrode.

In modern implantable cardioverter/defibrillators, the particular therapies are programmed into the device ahead of time by the physician, and a menu of therapies is typically provided. For example, on initial detection of an atrial or ventricular tachycardia, an anti-tachycardia pacing therapy may be selected and delivered to the chamber in which the tachycardia is diagnosed or to both chambers. On redetection of tachycardia, a more aggressive anti-tachycardia pacing therapy may be scheduled. If repeated attempts at anti-tachycardia pacing therapies fail, a higher level cardioversion pulse may be selected thereafter. Therapies for tachycardia termination may also vary with the rate of the detected tachycardia, with the therapies increasing in aggressiveness as the rate of the detected tachycardia increases. For example, fewer attempts at anti-tachycardia pacing may be undertaken prior to delivery of cardioversion pulses if the rate of the detected tachycardia is above a preset threshold. The references cited above in conjunction with descriptions of prior art tachycardia detection and treatment therapies are applicable here as well.

In the event that atrial or ventricular fibrillation is identified, the typical therapy will be delivery of a high amplitude defibrillation pulse, typically in excess of 10 joules in the case of ventricular fibrillation and about 1 joule or less in the case of atrial defibrillation. Lower energy levels will be employed for cardioversion. As in the case of currently available implantable pacemakers/cardioverter/ defibrillators, and as discussed in the above-cited references, it is envisioned that the amplitude of the defibrillation pulse may be incremented in response to failure of an initial pulse or pulses to terminate fibrillation. Prior art patents illustrating such pre-set therapy menus of anti-tachyarrhythmia therapies include the above-cited U.S. Pat. No. 4,830,006, issued to Haluska, et al., U.S. Pat. No. 4,726,380, issued to Vollmann et al. and U.S. Pat. No. 4,587,970, issued to Holley et al.

Figure 3:
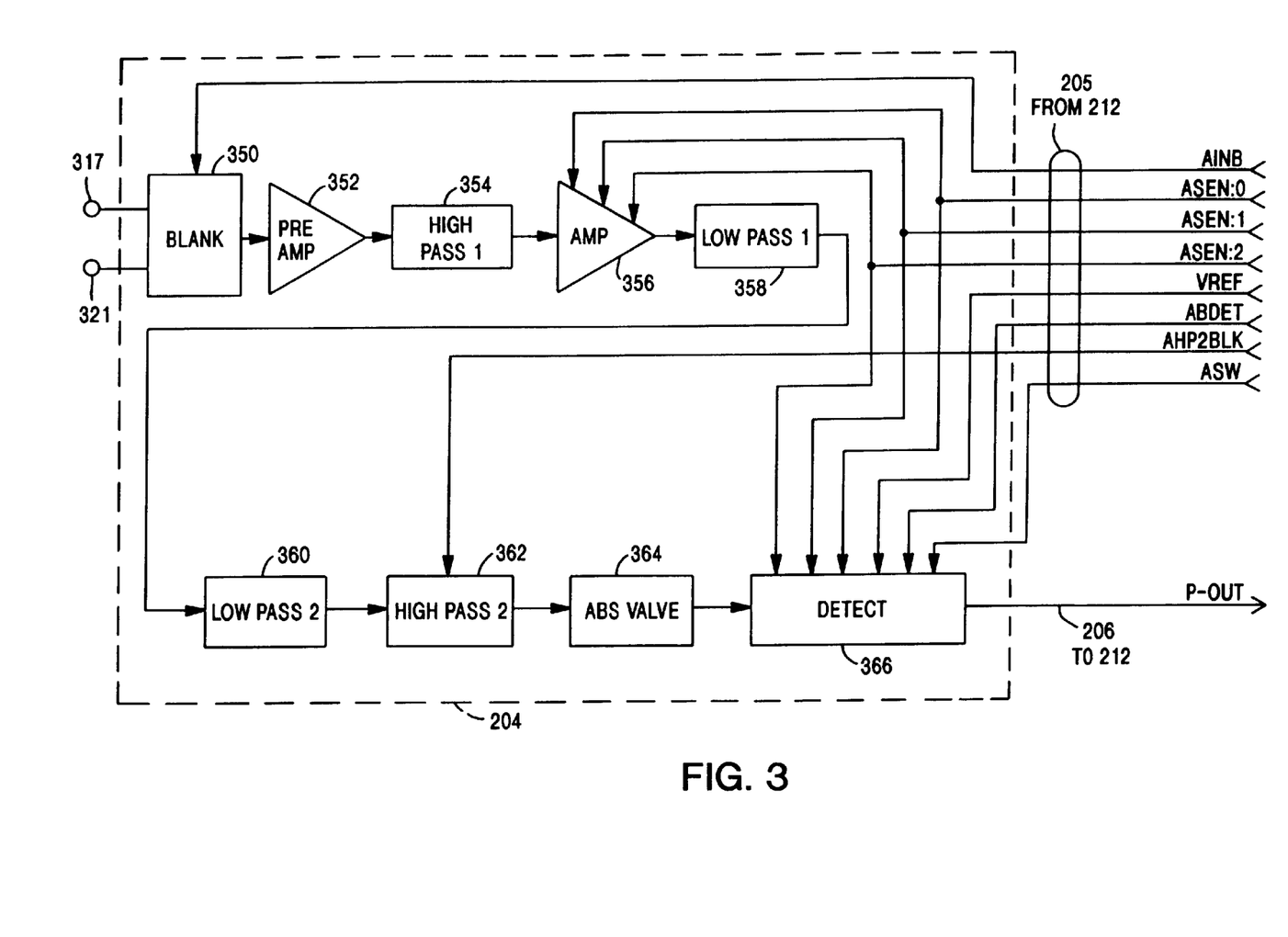
FIG. 3 is a functional schematic diagram of an atrial sense amplifier according to a first embodiment of the present invention.

FIG. 3 is a functional block diagram of amplifier 204 illustrated in FIG. 2. This diagram illustrates the basic functional components of the amplifier and their interconnection to the pacer timing/control circuitry 212. Signals from the ventricular electrodes 317 and 321 first pass through blanking switches 350, which operate to disconnect the amplifier from the electrodes during delivery of an atrial pacing pulse, during the duration of a ventricular input blanking signal on line AINB, which extends through the delivered atrial pacing pulse and during the fast recharge period thereafter. Depolarization signals passing through blanking switches 350 are amplified by preamp 352 and then pass through a first high pass filter 354. The high pass filtered signal is passed through an adjustable gain amplifier 356 which amplifies the signal by one of eight available multiplication factors under the control of digital signals on lines ASEN:0, ASEN:1 and ASEN:2. The degree of amplification determines the programmed base sensing threshold, as discussed below.

The amplified signal is passed on through a first low pass filter 358, a second low pass filter 360, a second high pass filter 362 and an absolute value circuit 364 which produces at its output the absolute value of the previously filtered and amplified signal. In response to a blanking signal on line AHP2BLK, passage of signals through high pass filter 362 is prohibited for defined periods of time following delivery of atrial and ventricular pacing pulses, providing an additional blanking function. The duration of blanking in conjunction with a delivered atrial pacing pulse is preferably the same as the blanking interval defined by the blanking signal on line AINB following delivery of an atrial pacing pulse. In conjunction with the delivery of an atrial pacing pulse, the blanking period may be greater, for example, forty or more milliseconds.

The output of the absolute value circuit 364 is provided to the detector circuit 366 which compares it to a defined sensing threshold to determine whether an P-wave is to be detected or not. If the signal exceeds the threshold, detector circuit 366 provides an output on P-OUT line 206, which is provided to pacer timing and control circuit 212 (FIG. 2). The sensing threshold defined by detector circuit 366 is variable, and is adjusted in response to sensed and paced ventricular events, delivered ventricular pacing pulses and delivered atrial pacing pulses. The detector 366, in conjunction with the programmed gain factor of amplifier 356 defines the programmed base sensing threshold which is normally in effect, and a variable sensing threshold effective after sensed ventricular events and delivered atrial and ventricular pacing pulses. In order to be detected as an P-wave, the signal from absolute value circuit 364 must exceed the greater of the base sensing threshold and the variable threshold, as discussed in more detail below. The duration and selection of the increased effective sensing threshold following delivered atrial pacing pulses is controlled by pacer timing/control circuitry via the ABDET and ASW lines. Adjustment of the effective sensing threshold following a delivered atrial pacing pulse and following a ventricular event preceded by a delivered atrial pacing pulse is accomplished by means of a reference voltage applied to the input of the detector 366 the line VREF and by the signal levels on the ASEN:0, ASEN:1 and ASEN:2 lines. Adjustment of the sensing threshold following a sensed P-wave and following a ventricular event preceded by a sensed P-wave is a function of the amplitude of the preceding sensed P-wave as reflected by the output of absolute value circuit 364 on the ABSVAL line.

Figure 4:
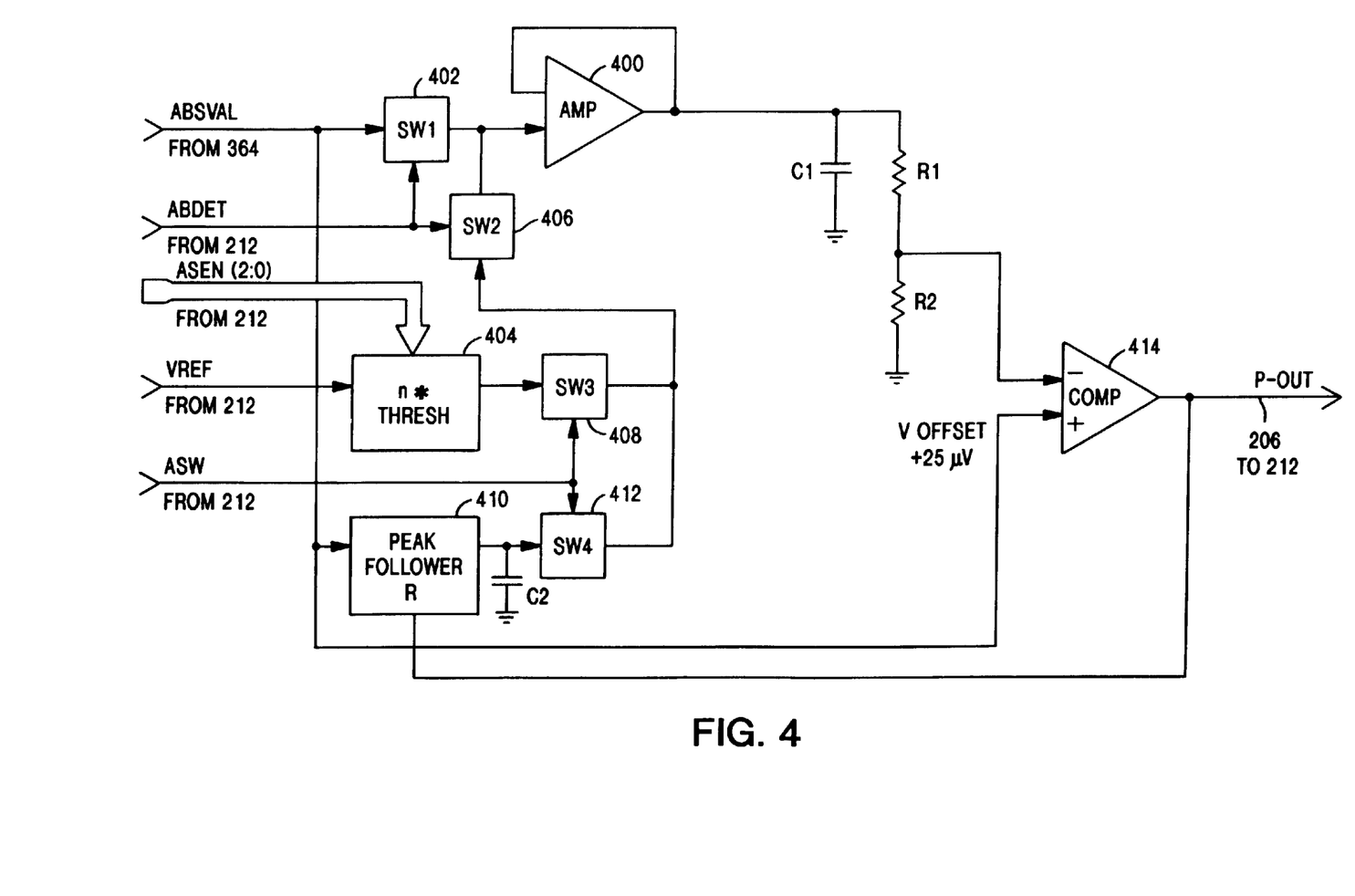
FIG. 4 is a functional schematic diagram of the automatic sensing threshold adjustment circuitry of the amplifier of FIG. 3.

FIG. 4 illustrates detector 366 in more detail, and illustrates the manner in which the detector works in conjunction with amplifier 356 to define the various effective sensing thresholds employed by the device. The amplified filtered P-wave signal on the ABSVAL line from absolute value circuit 364 (FIG. 3) is applied to a comparator 414 which, in conjunction with the remainder of the illustrated circuitry defines an adjustable sensing threshold. If the signal from the absolute value circuit exceeds the currently effective sensing threshold, a signal is generated on P-OUT line 206, which in turn is provided to the timing and control circuitry 212. The programmed base sensing threshold "S" is defined by the DC offset of the comparator circuit 414 in conjunction with the programmed amplification of the signal by amplifier 356. The effective sensing threshold is increased from the base threshold following sensed P-waves, ventricular events and delivered atrial pulses as follows.

As noted above, the signal on the ABSVAL line is applied to comparator 414 and, if it exceeds the then established sensing threshold, causes generation of a signal on P-OUT line 206 indicative of the sensing of a P-wave. In addition, the signal on line ABSVAL is also employed to set the sensing threshold after a sensed P-wave. The signal on line ABSVAL is applied to amplifier 400, configured as a non-inverting voltage follower, via switch 402 which is normally closed. The output of amplifier 400 is applied to capacitor C1, which, via resistors R1 and R2 defines the sensing threshold for comparator 414. The values of the components are chosen such that the voltage stored in capacitor C1 discharges over a time constant T1, which may be, for example, 100 milliseconds. Resistors R1 and R2 are sized so that the sensing threshold defined by capacitor C1 in conjunction with resistors R1 and R2 is a desired proportion, e.g. approximately 75%, of the peak amplitude of the sensed P-wave. In addition, the signal on the ABSVAL line is also applied to a resettable peak follower 410 which in response to a signal on P- OUT line 206 stores the peak amplitude of the signal,. Thus, in response to sensing of a signal which is identified as a P-wave, its amplitude is stored in peak follower 410, which retains the stored amplitude until a subsequent sensed P-wave. In response to a signal on P-OUT line 206, pacing timing and control circuitry 212 (FIG. 2) sets the line ABDET high for a period of time, for example 100 milliseconds, in turn opening switch 402 and closing switch 406. If not already low, pacing timing/control circuit 212 also sets line ASW low, in turn closing switch 412. The voltage stored in peak follower 410 is applied through switch 412 and switch 406 to amplifier 400 and thence to capacitor C1. Thus, following a sensed P-wave, the effective sensing threshold is set equal to a desired proportion of the peak amplitude of the P-wave for a period of time of approximately 100 milliseconds. At the expiration of this time interval, the line ABDET goes low, opening switch 406 and allowing capacitor C1 to discharge, whereby the effective sensing threshold thereafter decays back to the programmed base sensing threshold S. Should a ventricular event be sensed following a preceding sensed atrial event, pacing timing and controller circuit 212 again sets the ABDET line high, for example for a period of 120 milliseconds, defining an increased sensing threshold thereafter proportional to the amplitude previously sensed P-wave.

In response to a delivered atrial pacing pulse, pacing/timing controller 212 sets line ASW high until a subsequent P-wave. This in turn opens switch 412 and closes switch 408. The pacing/timing controller also sets line ABDET high for a period, for example, of 100 milliseconds, closing switch 406 and opening switch 402. Instead of applying the voltage stored in peak follower 410 to define an elevated sensing threshold after a delivered atrial pacing pulse, multiplier circuit 404 operates, under control of lines ASEN:0, ASEN:1 and ASEN:2 to define an output signal which is a predetermined multiple of the voltage on line VREF. This voltage is passed via switch 408 and switch 406 to amplifier 400, where it is applied to capacitor C1 to define a sensing threshold proportional to the output of the multiplier circuit 404. The value of the defined threshold preferably increases as a function of the programmed lower or base sensing threshold S. In a most preferred embodiment, the value of the defined increased threshold decreases a proportionally greater amount in conjunction with lower programmed base sensing thresholds, and increases by a relatively lesser amount, with respect to higher programmed base sensing thresholds. For example, at a programmed base sensing threshold of 0.1 millivolts, the defined increased threshold may be, for example, 0.9 millivolts. At a programmed sensing threshold of 0.6 millivolts, the defined increased sensing threshold may be 1.8 millivolts. At a programmed sensing threshold of 2.1 millivolts, the defined sensing threshold may also be 2.1 millivolts. This increased threshold persists for as long as the signal on line ABDET is high, and decays thereafter at a time constant T1 in a fashion analogous to the decay of the sensing threshold following a sensed atrial event. In the event of a paced or sensed ventricular event following a preceding atrial pacing pulse, the sensitivity threshold is again temporarily increased in response to the timing/control circuitry 212 setting line ABDET high, for example for a period of 120 milliseconds or more. The increased sensing threshold again persists until line ABDET goes low, after which the sensing threshold decays according to time constant T1 defined by capacitor C1 and resistors R1 and R2.

Figure 5:
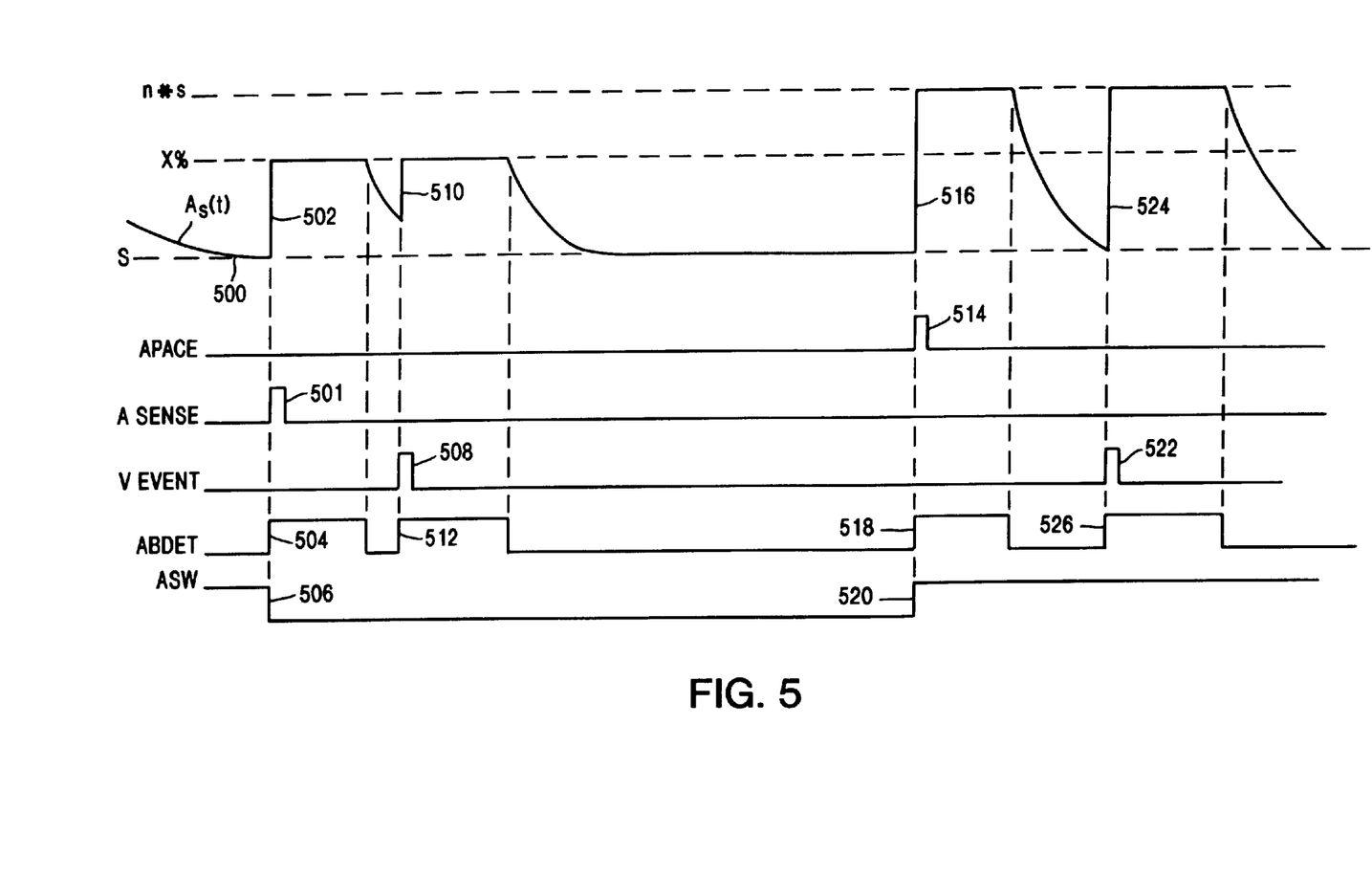
FIG. 5 is a timing diagram illustrating the operation of the circuitry of FIGS. 3 and 4.

FIG. 5 is a timing diagram illustrating the operation of the detector 366 (FIG. 3) to define the various variable sensing thresholds described above. The upper portion of FIG. 5 is a diagram illustrating the variable sensing threshold $A_s(t)$. The variable effective sensing threshold $A_s(t)$ is shown decaying to the base or lower sensing threshold S at 500.

At 501, a signal is generated on line P-OUT, 506, indicative of a sensed P-wave. This signal, as discussed above, causes pacemaker timing/control circuitry 212 to set line ABDET high at 504 and set line ASW low at 506. At 502, the effective atrial sensing threshold $A_s(t)$ is set equal to a predetermined percentage of the amplitude of the sensed P-wave which caused generation of the signal on line POUT at 501. This increased sensing threshold persists as discussed above until line ABDET goes low, 100 milliseconds later. Thereafter, the sensing threshold decays exponentially back to the lower or base sensing threshold S. A ventricular event 508 is illustrated occurring prior to the effective sensing threshold $A_s(t)$ returning to the base sensing threshold S. In response to the sensed or paced ventricular event at 508, pacing timing control circuitry sets line ABDET high at 512, for example for a period of 120 milliseconds. The sensing threshold $A_s(t)$ is increased at 510 to the same value as following the preceding sensed P-wave at 501, and persists at this level until pacing timing and control circuitry 212 sets line ABDET low again, after which the sensing threshold decays exponentially back to the base sensing threshold S.

At 514, an atrial pacing pulse is delivered which in turn causes pacing timing and control circuitry 212 to set line ABDET line high at 518 and line ASW high at 520. Line ASW will stay high until a subsequent sensed P-wave. As discussed above, as long as line ABDET is high, the effective sensing threshold is set to a preset multiple of the base or lower sensing threshold at 516, and stays at this increased threshold level until line ABDET goes low, for example 100 milliseconds thereafter. At 522, a ventricular event, sensed or paced, occurs again, increasing the effective sensing threshold $A_s(t)$ to the present multiple of the base sensing threshold S, and causing the pacing timing circuitry 212 to set line ABDET high at 524. The increased sensing threshold persists until line ABDET goes low, for example 120 milliseconds thereafter, after which the effect of sensing threshold decays back to the base sensing threshold S.

The operation of the amplifier according to the first embodiment of the present invention produces several benefits. By providing for an increased atrial sensing threshold following a delivered atrial pacing pulse as opposed to simply blanking the atrial amplifier, inappropriate sensing of the pacing pulse itself and of any post pacing polarization of the atrial electrodes is prevented, while sensing of P-waves closely spaced to the delivered atrial pacing pulse is facilitated. By providing for an increased atrial sensing threshold following a ventricular event, as opposed to simply blanking the atrial amplifier, inappropriate sensing of far-field R-waves is avoided, while sensing of P-waves is facilitated. By providing an increased sensitivity threshold level following a ventricular event which varies as a function of the preceding sensed atrial event, the accuracy of the amplifier in rejecting far-field R-waves is enhanced. By providing for an exponential decay of the increased threshold values, inappropriate atrial oversensing which might otherwise be associated with an abrupt change in sensing threshold is avoided.

Figure 6:
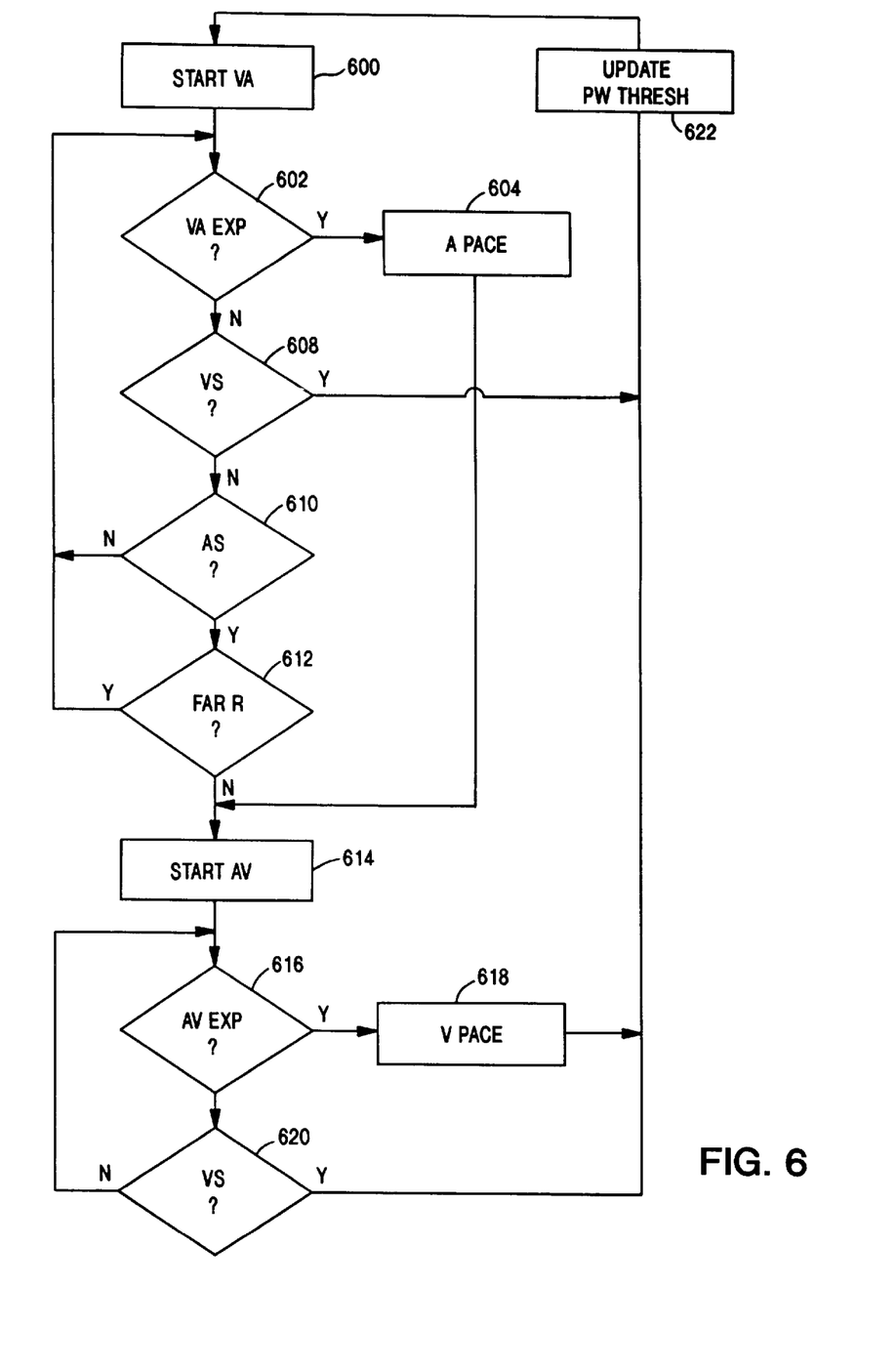
FIGS. 6, 7 and 8 are functional flow charts illustrating the operation of a pacemaker according to a second embodiment of the present invention.

FIG. 6 is a functional flow chart illustrating the operation of a second embodiment of a device practicing the present invention, implemented in a device as in FIG. 2. In this device, however, rather than implementing the far field R-wave rejection mechanism in hardware, the mechanism is instead implemented in the form of software stored in the read only memory associated with microprocessor 224 (FIG. 2). In this implementation of the invention, the atrial sense amplifier 204 (FIG. 2) may be a conventional sense amplifier, having a programmable sensing threshold correspond to the programmable base sensing threshold discussed above and provided with a blanking period following delivery of an atrial or ventricular pacing pulse. The atrial sense amplifier 204 may also adjust sensing thresholds following sensed and paced atrial events in the same manner as the amplifier in the first embodiment of the invention, discussed above. Adjustment of the effective P-wave sensing threshold in conjunction with occurrences of ventricular events is controlled by microprocessor 224 (FIG. 2) The effective sensing threshold is adjusted according to the mechanism illustrated in the flow chart of FIGS. 6–8. In conjunction with these flow charts, it should be understood that the device is operating as a conventional DDD type pacemaker, pacing and sensing in both the atrium and ventricles. Details of operation of the device not illustrated in the flow chart should be understood to conform to conventional DDD pacemakers, and are not discussed in detail herein.

Figure 7:
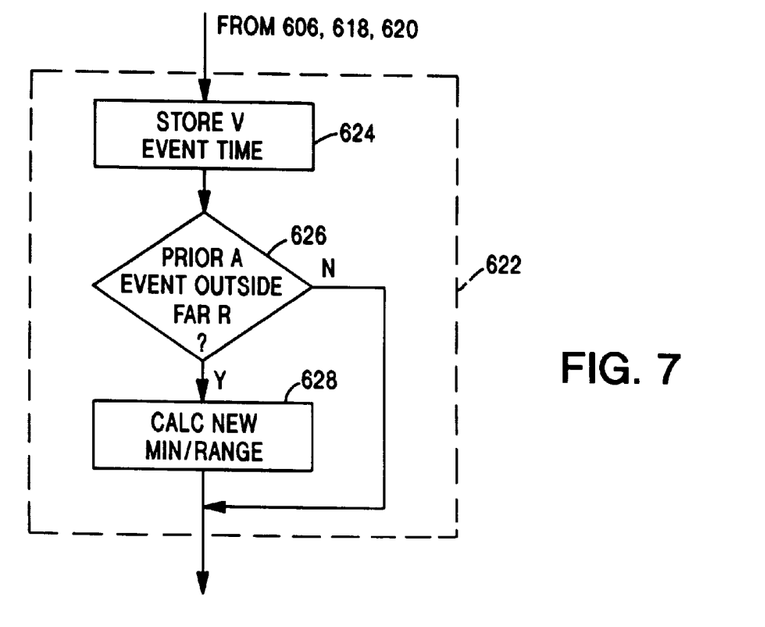
Figure 8:
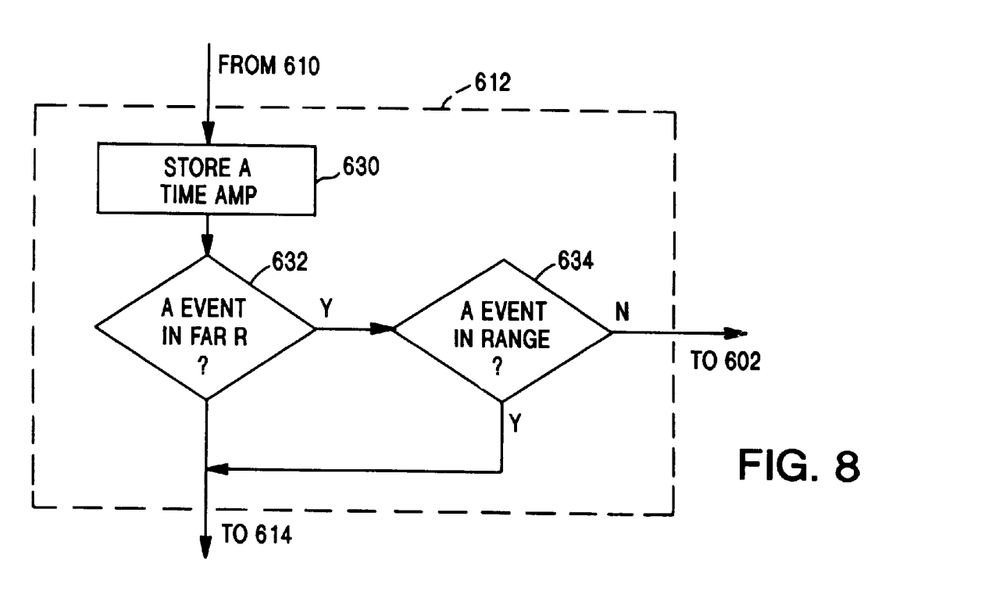

In the implementation illustrated in FIGS. 6–8, the device defines a far-R window beginning X milliseconds prior to a ventricular event and extending for a period of Y milliseconds thereafter. For example, the time interval may span 50 milliseconds prior to the ventricular event and extend for 100–150 milliseconds thereafter. During the portion of the far-R window following the ventricular event, the device defines an effective increased P-wave sensing threshold in an effort to reject far field R-wave signals as described in conjunction with the hardware implementation above. The P-wave sensing threshold is defined as a function of the amplitude of preceding P-waves, sensed outside of far-R windows, and may either be a simple minimum amplitude above which an atrial sensed event is considered to be a P-wave or may be a range of acceptable amplitudes, between which the amplitude of an atrial event sensed during the defined window must fall in order for the event to be considered to be a P-wave. The determination as to whether an event sensed by the atrial amplifier is a far field R-wave or a P-wave may be employed in conjunction with the arrhythmia detection algorithms. If the event is sensed within the Far-R time window, following a ventricular event, the sensed event will not be employed to initiate a new AV interval.

For convenience of description, the flow chart may be considered first at 600, concurrent with the initiation of the VA escape interval. During this time period, the device awaits either the expiration of the VA interval at 602, sensing of a ventricular event at 606 or sensing of an atrial event at 610. In the event the VA interval expires without sensing in the atrium or ventricle, an atrial pacing pulse is delivered at 604, and the AV interval is initiated at 614. In the event a ventricular depolarization is sensed by the ventricular sense amp at 606, the device determines at 622 whether it is appropriate to update the effective P-wave sensing threshold at 608, and the VA interval is reinitialized at 600. In the event that an atrial event is sensed at 610, the device checks at 612 to determine whether the signal might be indicative of a far field R-wave. In particular, the device determines whether the sensed atrial event occurred within the defined far-R window following the immediately preceding ventricular event and if so, whether it exceeds the minimum amplitude or falls within the defined amplitude range indicative of a P-wave. If the atrial event is sensed within the far-R window and is less than the minimum amplitude or outside the defined range, it is identified as a likely to be a far field R-wave and does not initiate an AV interval. The device continues to await expiration of the VA interval at 602, ventricular sensing at 606 and atrial sensing at 610. If the atrial event is sensed after the far-R window associated with the preceding ventricular event or is sensed within the window but is greater than the minimum amplitude or within the defined range, it is identified as a likely to be a P-wave and does initiate an AV interval at 614. The amplitude and time of the atrial event is stored the value may be used to update the effective P-wave sensing threshold employed during the far-R windows, as discussed below in conjunction with FIG. 7.

During the AV interval, the device awaits expiration of the AV interval at 616 or ventricular sensing at 620. In response to expiration of the AV interval at 616, the device delivers a ventricular pacing pulse at 618 and initiates the VA interval at 600. In response to ventricular sensing at 620, the device checks to determine whether an update to the effective P-wave sensing threshold during the far field R-wave window is appropriate at 622 and initiates the VA interval at 600.

FIG. 7 illustrates in more detail the mechanism by which the device determines at block 622 (FIG. 6), whether updating the effective P-wave sensing threshold for the far-R window is appropriate. Following the sensing of an R-wave or delivery of a ventricular pacing pulse, its time of occurrence is stored at 624, and the device checks at 626 to determine whether the preceding sensed atrial event was outside the far-R windows associated with the ventricular preceding and following the sensed atrial event. If so, the value of the preceding stored P-wave is employed to update the effective atrial sensing threshold applicable during the far field R-wave window. For example, the minimum amplitude indicative of a P-wave during the far field R-wave window may be set at a percentage, for example 75%, of the average amplitude of the preceding four to eight sensed atrial events sensed outside of the far field R-wave windows or a range extending from 75% of the average amplitude to 150% of the average amplitude may be defined. Like the hardware based embodiment described above, the device attempts to avoid employing the amplitudes of far field R-waves in setting effective atrial sensing thresholds.

FIG. 8 illustrates the operation of the device in determining whether a sensed P-wave is likely to be a far field R-wave, illustrating the operation of block 612 in FIG. 6 in more detail. At 630, the time and amplitude of the sensed event on the atrial lead is stored. At 632 the device checks to determine whether the atrial event fell within a far-R window associated with the preceding ventricular event. If so, the device further checks at 634 to determine whether the amplitude of the sensed atrial event exceeds the defined effective P-wave threshold for the far field R-wave window, or falls within the defined acceptable range of amplitudes. If so, the device treats the sensed event as a P-wave, initiating the AV interval at 614. While not discussed in detail herein, it should also be understood that the ability of a device operating according to the flow chart of FIGS. 6 through 8 to distinguish between P-waves and far field R-waves is also of particular value in the context of arrhythmia detection functions.

While the invention is described above in the context of a device which employs an atrial sense amplifier which provides for an automatically adjusted sensing threshold following sensed atrial events and following atrial pacing pulses, the present invention may also be usefully employed in the context of devices which do not adjust the effective sensing thresholds following either or both of such events. Further, while the disclosed embodiment of the invention takes the form of a microprocessor controlled device, the invention is of course equally useful in the context of a device in which the various time intervals employed to control the sensing thresholds are determined by hardware, for example by a digital circuit employing dedicated logic, or by analog timers. The specific mechanism by which the time intervals associated with the operation of the adjustable threshold function are defined is not critical to successful use and enjoyment of the present invention. As such, the above disclosure should be taken as exemplary, rather than limiting, with regard to the claims which follow.

In the claims:

1. An implantable cardiac pacemaker having means for sensing electrical signals in a patient's atrium and means for sensing depolarizations of the patient's ventricle, wherein the means for sensing electrical signals in the patient's atrium comprises:

means for defining a base atrial sensing threshold;

means for measuring amplitudes of electrical signals sensed in the patient's atrium;

means responsive to sensing a depolarization of the patient's ventricle following a signal sensed in the patient's atrium for defining a first increased atrial sensing threshold for a first time period thereafter, greater than the base atrial sensing threshold and based upon the measured amplitude of a previous electrical signal sensed in the patient's atrium.

2. A pacemaker according to claim 1 further comprising means for allowing the increased sensing threshold to decay to the base sensing threshold following expiration of the first time period.

3. A pacemaker according to claim 1 or claim 2 further comprising means for defining A–V intervals following those signals sensed in the patient's atrium during the first time periods only if the sense signals exceed the increased sensing threshold and means responsive to expirations of A–V intervals for delivering pacing pulses to the patient's ventricle.

4. A pacemaker according to claim 3 further comprising means for defining an A–V intervals following signals sensed in the patient's atrium after the first time periods which exceed the base sensing threshold.

5. A cardiac pacemaker having means for sensing electrical signals in a patient's atrium, means for delivering pacing pulses to the patient's atrium and means for sensing depolarizations of the patient's ventricle, wherein the means for sensing electrical signals in the patient's atrium comprises:

means for defining a base atrial sensing threshold;

means responsive to sensing a depolarization of the patient's ventricle following a preceding delivered atrial pacing pulse, for defining a first increased atrial sensing threshold for a first time period thereafter, greater than the base atrial sensing threshold.

6. A pacemaker according to claim 5 further comprising means for allowing the increased sensing threshold to decay to the base sensing threshold following expiration of the first time period.

7. A pacemaker according to claim 5 or claim 6 further comprising means for defining A–V intervals following those signals sensed in the patient's atrium during the first time periods only if the sense signals exceed the increased sensing threshold and means responsive to expirations of A–V intervals for delivering pacing pulses to the patient's ventricle.

8. A pacemaker according to claim 7 further comprising means for defining an A–V intervals following signals sensed in the patient's atrium after the first time periods which exceed the base sensing threshold.

9. A method of controlling effective atrial sensing thresholds in a cardiac pacemaker having an atrial sense amplifier and a ventricular sense amplifier, comprising the steps of:

defining a base atrial sensing threshold;

measuring amplitudes of electrical signals sensed in a patient's atrium;

responsive to sensing a depolarization of the patient's ventricle following a signal sensed in the patient's atrium, defining a first increased atrial sensing threshold for a first time period thereafter, greater than the base atrial sensing threshold and based upon the measured amplitude of a previous electrical signal sensed in the patient's atrium.

10. A method according to claim 9 further comprising the step of allowing the increased sensing threshold to decay to the base sensing threshold following expiration of the first time period.

11. A method according to claim 9 or claim 10 further comprising the steps of defining A–V intervals following those signals sensed in the patient's atrium during the first time periods only if the sense signals exceed the increased sensing threshold and responsive to expirations of A–V intervals delivering pacing pulses to the patient's ventricle.

12. A method according to claim 11 further comprising the step of defining an A–V intervals following signals sensed in the patient's atrium after the first time periods which exceed the base sensing threshold.

13. A method of controlling effective atrial sensing thresholds in a cardiac pacemaker having an atrial sense amplifier and a ventricular pacing pulse generator, comprising the steps of:

defining a base atrial sensing threshold;

responsive to sensing a depolarization of the patient's ventricle following a preceding delivered atrial pacing pulse, defining a first increased atrial sensing threshold for a first time period thereafter, greater than the base atrial sensing threshold.

14. A method according to claim 13 further comprising the step of allowing the increased sensing threshold to decay to the base sensing threshold following expiration of the first time period.

15. A method according to claim 13 or claim 14 further comprising the steps of defining A–V intervals following those signals sensed in the patient's atrium during the first time periods only if the sense signals exceed the increased sensing threshold and responsive to expirations of A–V intervals delivering pacing pulses to the patient's ventricle.

16. A method according to claim 15 further comprising the step of defining an A–V intervals following signals sensed in the patient's atrium after the first time periods which exceed the base sensing threshold.

* * * * *

UNITED STATES PATENT AND TRADEMARK OFFICE
CERTIFICATE OF CORRECTION

PATENT NO.   : 6,249,701 B1  
DATED        : June 19, 2001  
INVENTOR(S)  : Rajasekhar et al.

Page 1 of 1

It is certified that error appears in the above-identified patent and that said Letters Patent is hereby corrected as shown below:

<u>Title page,</u>
Item [57], in the ABSTRACT, please delete "A system and method is provided to view an anatomical structure such as a blood vessel in high contrast with its surrounding tissue. The system and method may be used to produce an image of an anatomical structure using reflected electromagnetic radiation singularly scattered from target tissue. The system and method may also provide same-side illumination and detection of reflected electromagnetic radiation in a convenient integral imaging device. The system and method may also provide helmet mounted imaging technology in a single integral helmet which allows the wearer to view an anatomical structure located within a patient such that the image is continuously oriented according to the orientation of the helmet wearer's head. The system and method may also be used in the performance of venipuncture. The system and method may provide for improved contrast between any anatomical structure and its surrounding tissue for use in any imaging system." and insert -- Far field R-wave sensing is implemented using a time window associated with a ventricular event. The atrial sensing threshold is adjusted from a predetermined or programmed base sensing threshold to a level that allows for appropriate sensing of P-waves in the atrium while eliminating an undesired sensing of far field R-waves. The atrial sensing threshold may be adjusted as a function of the amplitude of one or more preceding P-waves as sensed by the atrial-sense amplifier. Sensed atrial events, which lay beyond the increased sensing threshold, are identified as P-waves. --

Signed and Sealed this

Twenty-fifth Day of June, 2002

*Attest:*

*Attesting Officer*

JAMES E. ROGAN  
*Director of the United States Patent and Trademark Office*